United States Patent [19]
Amberg et al.

[11] Patent Number: 6,103,732
[45] Date of Patent: Aug. 15, 2000

[54] CARBOXYLIC ACID DERIVATIVES, THEIR PRODUCTION AND USE

[75] Inventors: Wilhelm Amberg, Friedrichsdorf; Andreas Kling, Mannheim; Dagmar Klinge, Heidelberg; Hartmut Riechers, Neustadt; Ernst Baumann, Dudenhofen; Liliane Unger, Ludwigshafen; Manfred Raschack, Weisenheim; Stefan Hergenröder, Mainz; Sabine Schult, Speyer, all of Germany

[73] Assignee: BASF Aktiengesellschaft, Ludwigshafen, Germany

[21] Appl. No.: 09/155,948

[22] PCT Filed: Apr. 4, 1997

[86] PCT No.: PCT/EP97/01687

§ 371 Date: Oct. 8, 1998

§ 102(e) Date: Oct. 8, 1998

[87] PCT Pub. No.: WO97/38982

PCT Pub. Date: Oct. 23, 1997

[30] Foreign Application Priority Data

Apr. 12, 1996 [DE] Germany .......................... 196 14 542

[51] Int. Cl.[7] .................. A61K 31/44; A61K 31/505; C07D 213/68; C07D 239/34
[52] U.S. Cl. .................. 514/269; 514/274; 514/312; 514/345; 514/348; 514/349; 544/302; 544/314; 544/319; 546/141; 546/157; 546/158; 546/296; 546/301; 546/302

[58] Field of Search ....................... 544/302, 314, 544/319; 546/157, 158, 141, 296, 301, 302; 514/269, 274, 312, 345, 348, 349

[56] References Cited

FOREIGN PATENT DOCUMENTS

96/00219  1/1996  WIPO .

*Primary Examiner*—Mukund J. Shah
*Assistant Examiner*—V. Balasubramanian
*Attorney, Agent, or Firm*—Keil & Weinkauf

[57] ABSTRACT

Carboxylic acid derivatives of the formula I

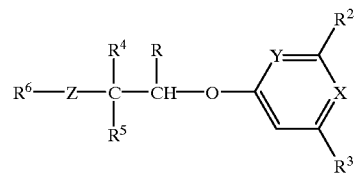

where the radicals have the meanings stated in the description, and the preparation of these agreements [sic] and their use as drugs are described.

10 Claims, No Drawings

CARBOXYLIC ACID DERIVATIVES, THEIR PRODUCTION AND USE

This application is a 371 of PCT/EP97/01687, filed Apr. 4, 1997.

The present invention relates to novel carboxylic acid derivatives, to their preparation and to their use.

Endothelin is a peptide which is composed of 21 amino acids and is synthesized and released by the vascular endothelium. Endothelin exists in three isoforms, ET-1, ET-2 and ET-3. In the following text, "Endothelin" or "ET" signifies one or all isoforms of endothelin. Endothelin is a potent vasoconstrictor and has a potent effect on vessel tone. It is known that this vasoconstriction is caused by binding of endothelin to its receptor (Nature, 332, 1988, 411–415; FEBS Letters, 231, 1988, 440–444 und Biochem. Biophys. Res. Commun., 154, 1988, 868–875).

Increased or abnormal release of endothelin causes persistent vasoconstriction in the peripheral, renal and cerebral blood vessels, which may lead to illnesses. It has been reported in the literature that elevated plasma levels of endothelin were found in patients with hypertension, acute myocardial infarct, pulmonary hypertension, Raynaud's syndrome, atherosclerosis and in the airways of asthmatics (Japan J. Hypertension, 12, (1989), 79, J. Vascular Med. Biology 2, (1990) 207, J. Am. Med. Association 264, (1990) 2868).

Accordingly, substances which specifically inhibit the binding of endothelin to the receptor ought also to antagonize the various abovementioned physiological effects of endothelin and therefore be valuable drugs.

We have found that certain carboxylic acid derivatives are good inhibitors of endothelin receptors.

The invention relates to carboxylic derivatives of the formula I

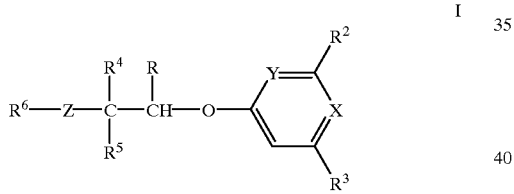

where R is tetrazole, nitrile, a group COOH or a radical which can be hydrolyzed to COOH, and the other substituents have the following meanings:

$R^2$ hydrogen, hydroxyl, $NH_2$, $NH(C_1-C_4\text{-alkyl})$, $N(C_1-C_4\text{-alkyl})_2$, halogen, $C_1-C_4$-alkyl, $C_1-C_4$-haloalkyl, $C_1-C_4$-alkoxy, $C_1-C_4$-haloalkoxy or $C_1-C_4$-alkylthio, or $CR^2$ is linked to $CR^{12}$ as indicated below to form a 5- or 6-membered ring;

X nitrogen or $CR^{12}$ where $R^{12}$ is hydrogen or $C_{1-5}$-alkyl, or $CR^{12}$ forms together with $CR^2$ or $CR^3$ a 5- or 6-membered alkylene or alkenylene ring which can be substituted by one or two $C_{1-4}$-alkyl groups and in which in each case one methylene group can be replaced by oxygen, sulfur, —NH or —N$C_{1-4}$-alkyl;

Y nitrogen or methine;

$R^3$ hydrogen, hydroxyl, $NH_2$, $NH(C_1-C_4\text{-alkyl})$, $N(C_1-C_4\text{-alkyl})_2$, halogen, $C_1-C_4$-alkyl, $C_1-C_4$-haloalkyl, $C_1-C_4$-alkoxy, $C_1-C_4$-haloalkoxy, —NH—O—$C_{1-4}$-alkyl, $C_1-C_4$-alkylthio; or $CR^3$ is linked to $CR^{12}$ as indicated above to form a 5- or 6-membered ring;

$R^4$ and $R^5$ (which can be identical or different):
phenyl or naphthyl, each of which can be substituted by one or more of the following radicals: halogen, nitro, cyano, hydroxyl, $C_1-C_4$-alkyl, $C_1-C_4$-haloalkyl, $C_1-C_4$-alkoxy, $C_1-C_4$-haloalkoxy, phenoxy, $C_1-C_4$-alkylthio, amino, $C_1-C_4$-alkylamino or $C_1-C_4$-dialkylamino; or phenyl or naphthyl, which are connected together in ortho positions by a direct linkage, a methylene, ethylene or ethenylene group, an oxygen or sulfur atom or an $SO_2$—, NH— or N-alkyl group, or $C_3-C_7$-cycloalkyl;

$R^6$ hydrogen, $C_1-C_8$-alkyl, $C_3-C_6$-alkenyl, $C_3-C_6$-alkynyl or $C_3-C_8$-cycloalkyl, it being possible for each of these radicals to be substituted one or more times by: halogen, hydroxyl, mercapto, carboxyl, nitro, cyano, $C_1-C_4$-alkoxy, $C_3-C_6$-alkenyloxy, $C_3-C_6$-alkynyloxy, $C_1-C_4$-alkylthio, $C_1-C_4$-haloalkoxy, $C_1-C_4$-alkylcarbonyl, $C_1-C_4$-alkoxycarbonyl, $C_{3-8}$-alkylcarbonylalkyl, $C_1-C_4$-alkylamino, di-$C_1-C_4$-alkylamino, phenyl or phenoxy or phenyl, substituted one or more times, e.g. once to three times, by halogen, nitro, cyano, $C_1-C_4$-alkyl, $C_1-C_4$-haloalkyl, $C_1-C_4$-alkoxy, $C_1-C_4$-haloalkoxy or $C_1-C_4$-alkylthio;

phenyl or naphthyl, each of which can be substituted by one or more of the following radicals: halogen, nitro, cyano, hydroxyl, amino, $C_1-C_4$-alkyl, $C_1-C_4$-haloalkyl, $C_1-C_4$-alkoxy, $C_1-C_4$-haloalkoxy, phenoxy, $C_1-C_4$-alkylthio, $C_1-C_4$-alkylamino, $C_1-C_4$-dialkylamino, dioxomethylene or dioxoethylene;

a five- or six-membered heteroaromatic system which contains one to three nitrogen atoms and/or one sulfur or oxygen atom and which can carry one to four halogen atoms and/or one or two of the following radicals: $C_1-C_4$-alkyl, $C_1-C_4$-haloalkyl, $C_1-C_4$-alkoxy, $C_1-C_4$-haloalkoxy, $C_1-C_4$-alkylthio, phenyl, phenoxy or phenylcarbonyl, it being possible for the phenyl radicals in turn to carry one to five halogen atoms and/or one to three of the following radicals: $C_1-C_4$-alkyl, $C_1-C_4$-haloalkyl, $C_1-C_4$-alkoxy, $C_1-C_4$-haloalkoxy and/or $C_1-C_4$-alkylthio;

Z sulfur or oxygen.

The compounds, and the intermediates for preparing them, such as II and IV, may have one or more asymmetrically substituted carbon atoms. Such compounds may be in the form of the pure enantiomers or pure diastereomers or a mixture thereof. The use of an enantiomerically pure compound as active substance is preferred.

The invention furthermore relates to the use of the abovementioned carboxylic acid derivatives for producing drugs, in particular for producing endothelin receptor inhibitors.

Compounds of the general formula IV where Z is sulfur or oxygen can be prepared, also in enantiomerically pure form, as described in P 44 36 851.8.

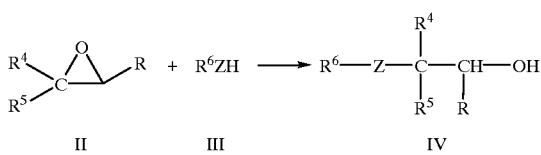

Compounds according to the invention in which the substituents have the meanings stated under the general formula I can be prepared, for example, by reacting the carboxylic acid derivatives of the general formula IV in which the substituents have the stated meanings with compounds of the general formula V,

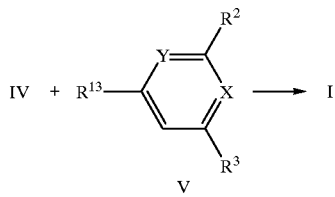

where $R^{13}$ is halogen or $R^{14}$—$SO_2$—, where $R^{14}$ can be $C_1$–$C_4$-alkyl, $C_1$–$C_4$-haloalkyl or phenyl. The reaction preferably takes place in an inert solvent or diluent with the addition of a suitable base, i.e. a base which deproteinates the intermediate IV, at a temperature in the range from room temperature to the boiling point of the solvent.

Examples of such solvents or diluents are aliphatic, alicyclic and aromatic hydrocarbons, each of which may be chlorinated, such as hexane, cyclohexane, petroleum ether, naphtha, benzene, toluene, xylene, methylene chloride, chloroform, carbon tetrachloride, ethyl chloride and trichloroethylene, ethers such as diisopropyl ether, dibutyl ether, methyl tert-butyl ether, propylene oxide, dioxane and tetrahydrofuran, nitrites, such as acetonitrile and propionitrile, acid amides such as dimethylformamide, dimethylacetamide and N-methylpyrrolidone, sulfoxides and sulfones, such as dimethyl sulfoxide and sulfolane.

Compounds of the formula V are known, and some of them can be bought, or they can be prepared in a conventional manner.

The base which can be used is an alkali metal or alkaline earth metal hydride such as sodium hydride, potassium hydride or calcium hydride, a carbonate such as an alkali metal carbonate, e.g. sodium or potassium carbonate, an alkali metal or alkaline earth metal hydroxide such as sodium or potassium hydroxide, an organometallic compound such as butyllithium, or an alkali metal amide such as lithium diisopropylamide.

Compounds of the formula I can also be prepared by starting from the corresponding carboxylic acids, i.e. compounds of the formula I where R is COOH, and first converting the latter in a conventional way into an activated form, such as an acid halide, an anhydride or imidazolide, and then reacting the latter with an appropriate hydroxyl compound $HOR^8$. This reaction can be carried out in conventional solvents and often requires the addition of a base, in which case the abovementioned are suitable. These two steps can also be simplified, for example, by allowing the carboxylic acid to act on the hydroxyl compound in the presence of a dehydrating agent such as a carbodiimide.

Moreover, compounds of the formula I can also be prepared by starting from salts of the corresponding carboxylic acids, i.e. from compounds of the formula I where R is a group $COR^1$ and $R^1$ is OM, where M can be an alkali metal cation or the equivalent of an alkaline earth metal cation. These salts can be reacted with many compounds of the formula $R^1$—A where A is a conventional nucleofugic leaving group, for example halogen such as chlorine, bromine, iodine or unsubstituted or halogen-, alkyl- or haloalkyl-substituted aryl- or alkylsulfonyl, such as toluenesulfonyl and methylsulfonyl, or another equivalent leaving group. Compounds of the formula $R^1$—A with a reactive substituent A are known or can easily be obtained with general expert knowledge. This reaction can be carried out in conventional solvents and advantageously takes place with the addition of a base, in which case the abovementioned are suitable.

The radical R in formula I can be varied widely. R is, for example, a group

where $R^1$ has the following meanings:
a) hydrogen;
b) a succinylimidoxy group;
c) a 5-membered heteroaromatic system linked via a nitrogen atom, such as pyrrolyl, pyrazolyl, imidazolyl and triazolyl, which may then carry one or two halogen atoms or one or two $C_1$–$C_4$-alkyl or one or two $C_1$–$C_4$-alkoxy groups.
d) $R^1$ is furthermore a group

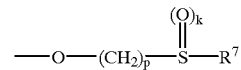

where k can assume the values 0, 1 and 2, p can assume the values 1, 2, 3 and 4, and $R^7$ is $C_1$–$C_4$-alkyl, $C_3$–$C_7$-cycloalkyl, $C_3$–$C_6$-alkenyl, $C_3$–$C_6$-alkynyl or unsubstituted or substituted phenyl which can be substituted by one or more, e.g. one to three, of the following radicals: halogen, nitro, cyano, $C_1$–$C_4$-alkyl, $C_1$–$C_4$-haloalkyl, hydroxyl, $C_1$–$C_4$-alkoxy, $C_1$–$C_4$-alkylthio, mercapto, amino, $C_1$–$C_4$-alkylamino, $C_1$–$C_4$-dialkylamino;

$R^1$ is furthermore a radical $OR^8$ where $R^8$ is:
hydrogen, the cation of an alkali metal such as lithium, sodium, potassium, or the cation of an alkaline earth metal such as calcium, magnesium and barium or a physiologically tolerated organic ammonium ion such as tertiary $C_1$–$C_4$-alkylammonium or the ammonium ion;
$C_3$–$C_8$-cycloalkyl such as cyclopropyl, cyclobutyl, cyclopentyl, cyclohexyl and cycloheptyl, cyclooctyl,
$C_1$–$C_8$-alkyl, in particular $C_1$–$C_4$-alkyl such as methyl, ethyl, n-propyl, isopropyl, n-butyl, isobutyl, tert-butyl;
$CH_2$-phenyl, which may be substituted by one or more of the following radicals: halogen, nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, $C_1$–$C_4$-alkylamino, $C_1$–$C_4$-dialkylamino, a $C_3$–$C_6$-alkenyl or $C_3$–$C_6$-alkynyl group, it being possible for this group in turn to carry one to five halogen atoms;
$R^8$ can furthermore be a phenyl radical which can carry one to five halogen atoms and/or one to three of the following radicals: nitro, cyano, $C_1$–$C_4$-alkyl, $C_1$–$C_4$-haloalkyl, hydroxyl, $C_1$–$C_4$-alkoxy, mercapto, $C_1$–$C_4$-alkylthio, amino, $C_1$–$C_4$-alkylamino, $C_1$–$C_4$-dialkylamino;
a 5-membered heteroaromatic system which is linked via a nitrogen atom and contains one to three nitrogen atoms and which can carry one or two halogen atoms and/or one or two of the following radicals: $C_1$–$C_4$-alkyl, $C_1$–$C_4$-haloalkyl, $C_1$–$C_4$-alkoxy, phenyl, $C_1$–$C_4$-haloalkoxy and/or $C_1$–$C_4$-alkylthio. Particular mention may be made of 1-pyrazolyl, 3-methyl-1-pyrazolyl, 4-methyl-1-pyrazolyl, 3,5-dimethyl-1-pyrazolyl, 3-phenyl-1-pyrazolyl, 4-phenyl-1-pyrazolyl, 4-chloro-1-pyrazolyl, 4-bromo-1-pyrazolyl, 1-imidazolyl, 1-benzimidazolyl, 1,2,4-triazol-1-yl, 3-methyl-1,2, 4-triazol-1-yl, 5-methyl-1,2,4-triazol-1-yl, 1-benzotriazolyl, 3,4-dichloro-1-imidazolyl;

f) $R^1$ is furthermore a radical

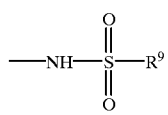

where $R^9$ is:
$C_1$–$C_4$-alkyl, $C_3$–$C_6$-alkenyl, $C_3$–$C_6$-alkynyl, $C_3$–$C_8$-cycloalkyl as mentioned above in particular, it being possible for these radicals to carry a $C_1$–$C_4$-alkoxy, $C_1$–$C_4$-alkylthio and/or a phenyl radical as mentioned above;
phenyl, unsubstituted or substituted, in particular as mentioned above;

g) $R^1$ is a radical

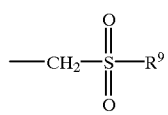

where $R^9$ has the abovementioned meaning;

h) $R^1$ can furthermore be

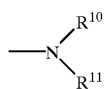

where $R^{10}$ and $R^{11}$ can be identical or different and have the following meanings:
hydrogen, $C_1$–$C_7$-alkyl, $C_3$–$C_7$-cycloalkyl, $C_3$–$C_7$-alkenyl, $C_3$–$C_7$-alkynyl, benzyl, phenyl, unsubstituted or substituted, as described above,
or $R^{10}$ and $R^{11}$ together form a $C_4$–$C_7$-alkylene chain which is closed to form a ring, is unsubstituted or substituted, e.g. substituted by $C_1$–$C_4$-alkyl, and may contain a heteroatom, e.g. oxygen, sulfur or nitrogen, such as —(CH$_2$)$_4$—, —(CH$_2$)$_5$—, —(CH$_2$)$_6$—, —(CH$_2$)$_7$—, —(CH$_2$)$_2$—O—(CH$_2$)$_2$—, —CH$_2$—S—(CH$_2$)$_2$—, —CH$_2$—NH—(CH$_2$)$_2$—, —(CH$_2$)$_2$13 N—(CH$_2$)$_2$—.

With a view to the biological effect, preferred carboxylic acid derivatives of the general formula I, both as pure enantiomers and pure diastereomers or as mixtures thereof, are those where the substituents have the following meanings:

$R^2$ hydrogen, hydroxyl, N($C_1$–$C_4$-alkyl)$_2$, the $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio groups and halogen atoms specifically mentioned for $R^1$, in particular chlorine, methyl, methoxy, ethoxy, difluoromethoxy and trifluoromethoxy, or $CR^2$ is linked to $CR^{12}$ as indicated below to form a 5- or 6-membered ring;

x nitrogen or $CR^{12}$, where $R^{12}$ is hydrogen or alkyl, or $CR^{12}$ forms together with $CR^2$ or $CR^3$ a 5- to 6-membered alkylene or alkenylene ring in which, in each case, a methylene group can be replaced by oxygen or sulfur, such as —CH$_2$—CH$_2$—CH$_2$—O—, —CH=CH—O—, —CH$_2$—CH$_2$—CH$_2$—O—, —CH=CH—CH$_2$O—, in particular hydrogen, —CH$_2$—CH$_2$—O—, —CH(CH$_3$)—CH(CH$_3$)—O—, —C(CH$_3$)=C(CH$_3$)—O—, —CH=C(CH$_3$)—O— or —C(CH$_3$)=C(CH$_3$)—S—;

Y nitrogen or methine;

$R^3$ hydrogen, hydroxyl, N($C_1$–$C_4$-alkyl)$_2$, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio groups and halogen atoms, in particular chlorine, methyl, methoxy, ethoxy, difluoromethoxy and trifluoromethoxy, or C—$R^3$ is linked to C—$R^{12}$ as mentioned above to form a 5- or 6-membered ring;

$R^4$ and $R^5$, which may be identical or different, phenyl or naphthyl, each of which may be substituted by one or more, e.g. one to three, of the following radicals: halogen, nitro, cyano, hydroxyl, mercapto, amino, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-alkylamino, di-$C_1$–$C_4$-alkylamino, $C_1$–$C_4$-alkylcarbonyl, $C_1$–$C_4$-alkoxycarbonyl; phenyl or naphthyl, which may be connected together in ortho positions by a direct linkage, a methylene, ethylene or ethenylene group, an oxygen or sulfur atom or an $SO_2$, NH or N-alkyl group, or $C_3$–$C_7$ cycloalkyl;

$R^6$ $C_1$–$C_8$-alkyl, $C_3$–$C_6$-alkenyl, $C_3$–$C_6$-alkynyl or $C_3$–$C_8$-cycloalkyl as mentioned above in particular, it being possible for each of these radicals to be substituted one or more times by: halogen, hydroxyl, mercapto, carboxyl, nitro, cyano,
$C_1$–$C_4$-alkoxy, $C_3$–$C_6$-alkenyloxy, $C_3$–$C_6$-alkynyloxy, $C_1$–$C_4$-alkylthio, $C_1$–$C_4$-haloalkoxy, $C_1$–$C_4$-alkylcarbonyl, hydroxycarbonyl, $C_1$–$C_4$-alkoxycarbonyl, $C_1$–$C_4$-alkylamino, di-$C_1$–$C_4$-alkylamino or unsubstituted or substituted phenyl or phenoxy, as mentioned above in particular;
phenyl or naphthyl, which can be substituted by one or more of the following radicals: halogen, nitro, cyano, hydroxyl, amino, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, $C_1$–$C_4$-alkylamino or $C_1$–$C_4$-dialkylamino;
a five- or six-membered heteroaromatic system which contains one to three nitrogen atoms and/or one sulfur or oxygen atom and which can carry one to four halogen atoms and/or one or two of the following radicals: $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, phenyl, phenoxy or phenylcarbonyl, it being possible for the phenyl radicals in turn to carry one to five halogen atoms and/or one to three of the following radicals: $C_1$–$C_4$-alkyl, $C_1$–$C_4$-haloalkyl, $C_1$–$C_4$-alkoxy, $C_1$–$C_4$-haloalkoxy and/or $C_1$–$C_4$-alkylthio, as mentioned for $R^4$ in particular;

Z sulfur or oxygen.

Particularly preferred compounds of the formula I, both as pure enantiomers and pure diastereomers or as mixture thereof, are those in which the substituents have the following meanings:

$R^2$ $C_1$–$C_4$-alkyl, $C_1$–$C_4$-alkoxy, $C_1$–$C_4$-alkylthio, trifluoromethyl or is linked to $R^{12}$ as mentioned below to form a 5- or 6-membered ring;

X nitrogen or $CR^{12}$, where $R^{12}$ is hydrogen or alkyl, or $CR^{12}$ forms together with $CR^2$ or $CR^3$ a 4- to 5-membered alkylene or alkenylene ring, e.g. —CH$_2$—CH$_2$—CH$_2$— or —CH=CH—CH$_2$—, in which, in each case, one methylene group can be replaced by oxygen or sulfur, such as —CH$_2$—CH$_2$—O—, —CH=CH—O—, —$CH_2$—$CH_2$—$CH_2$—O—, —CH=CH—$CH_2O$—, in particular hydrogen, —$CH_2$—$CH_2$—O—, —CH($CH_3$)—CH($CH_3$)—O—, —C($CH_3$)=C($CH_3$)—O—, —CH=C($CH_3$)—O— or —C($CH_3$)=C($CH_3$)—S;

Y nitrogen or methine;

$R^3$ the $C_1$–$C_4$-alkyl, $C_1$–$C_4$-alkoxy, $C_1$–$C_4$-alkylthio groups mentioned for $R^1$ or C—$R^3$ is linked to C—$R^{12}$ as mentioned above to form a 5- or 6-membered ring;

$R^4$ and $R^5$ phenyl (identical or different), which may be substituted by one or more, e.g. one to three, of the following radicals: halogen, nitro, hydroxyl, $C_1$–$C_4$-alkyl, $C_1$–$C_4$-alkoxy, $C_1$–$C_4$-alkylthio or $R^4$ and $R^5$ are phenyl groups which are connected together in ortho positions by a direct linkage, a methylene, ethylene or ethenylene group, an oxygen or sulfur atom or an $SO_2$, NH or N-alkyl group; or $R^4$ and $R^5$ are $C_3$–$C_7$-cycloalkyl;

$R^6$ $C_1$–$C_8$-alkyl, $C_3$–$C_6$-alkenyl or $C_3$–$C_8$-cycloalkyl, it being possible for each of these radicals to be substituted one or more times by: halogen, mercapto, caboxyl [sic], hydroxyl, nitro, cyano, $C_1$–$C_4$-alkoxy, $C_3$–$C_6$-alkenyloxy, $C_1$–$C_4$-alkylthio;

phenyl or naphthyl, which can be substituted by one or more of the following radicals: halogen, nitro, cyano, hydroxyl, amino, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, $C_1$–$C_4$-akylamino or $C_1$–$C_4$-dialkylamino;

a five- or six-membered heteroaromatic system which contains a nitrogen atom and/or a sulfur or oxygen atom and which can carry one to four halogen atoms and/or one or two of the following radicals: $C_1$–$C_4$-alkyl, $C_1$–$C_4$-haloalkyl, $C_1$–$C_4$-alkoxy, $C_1$–$C_4$-alkylthio, phenyl, phenoxy or phenylcarbonyl, it being possible for the phenyl radicals in turn to carry one to five halogen atoms and/or one to three of the following radicals: $C_1$–$C_4$-alkyl, $C_1$–$C_4$-haloalkyl, $C_1$–$C_4$-alkoxy and/or $C_1$–$C_4$-alkylthio;

Z sulfur or oxygen.

Examples of preferred compounds are listed in the following table.

TABLE I

[sic]

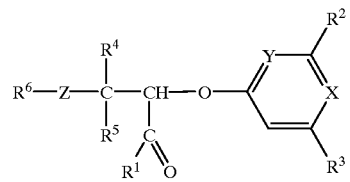

| No. | $R^1$ | $R^4$, $R^5$ | $R^6$ | $R^3$ | $R^2$ | X | Y | Z |
|---|---|---|---|---|---|---|---|---|
| I-1 | OH | phenyl | methyl | OMe | OMe | N | N | O |
| I-2 | OH | phenyl | methyl | OMe | Me | N | N | O |
| I-3 | OH | phenyl | methyl | Me | OMe | N | N | O |
| I-4 | OH | phenyl | methyl | ethyl | Me | N | N | O |
| I-5 | OH | phenyl | methyl | Me | ethyl | N | N | O |
| I-6 | OH | phenyl | methyl | Me | Me | N | N | O |
| I-7 | OH | phenyl | methyl | OMe | SMe | N | N | O |
| I-8 | OH | phenyl | methyl | OMe | $CF_3$ | N | N | O |
| I-9 | OH | phenyl | methyl | OMe | OMe | N | N | S |
| I-10 | OH | phenyl | methyl | OMe | Me | N | N | S |
| I-11 | OH | phenyl | methyl | Me | OMe | N | N | S |
| I-12 | OH | phenyl | methyl | ethyl | Me | N | N | S |
| I-13 | OH | phenyl | ethyl | OMe | OMe | N | N | O |
| I-14 | OH | phenyl | ethyl | OMe | Me | N | N | O |
| I-15 | OH | phenyl | ethyl | Me | OMe | N | N | O |
| I-16 | OH | phenyl | ethyl | ethyl | Me | N | N | O |
| I-17 | OH | phenyl | ethyl | Me | ethyl | N | N | O |
| I-18 | OH | phenyl | HO—$CH_2$—$CH_2$— | OMe | OMe | N | N | O |
| I-19 | OH | phenyl | HO—$CH_2$—$CH_2$— | OMe | Me | N | N | O |
| I-20 | OH | phenyl | HO—$CH_2$—$CH_2$— | Me | OMe | N | N | O |
| I-21 | OH | phenyl | HO—$CH_2$—$CH_2$— | ethyl | Me | N | N | O |
| I-22 | OH | phenyl | HO—$CH_2$—$CH_2$— | Me | ethyl | N | N | O |
| I-23 | OH | phenyl | HO—$CH_2$—$CH_2$— | Me | Me | N | N | O |
| I-24 | OH | phenyl | HO—$CH_2$—$CH_2$— | OMe | SMe | N | N | O |
| I-25 | OH | phenyl | $HO_2C$—$(CH_2)_2$— | OMe | OMe | N | N | O |
| I-26 | OH | phenyl | $HO_2C$—$(CH_2)_2$— | OMe | Me | N | N | O |
| I-27 | OH | phenyl | $HO_2C$—$(CH_2)_2$— | Me | OMe | N | N | O |
| I-28 | OH | phenyl | $HO_2C$—$(CH_2)_2$— | ethyl | Me | N | N | O |
| I-29 | OH | phenyl | $HO_2C$—$(CH_2)_2$— | Me | ethyl | N | N | O |
| I-30 | OH | phenyl | $HO_2C$—$(CH_2)_2$— | Me | Me | N | N | O |
| I-31 | OH | phenyl | $HO_2C$—$(CH_2)_2$— | OMe | SMe | N | N | O |
| I-32 | OH | phenyl | $HO_2C$—$CH_2$— | OMe | OMe | N | N | O |
| I-33 | OH | phenyl | $HO_2C$—$CH_2$— | OMe | Me | N | N | O |
| I-34 | OH | phenyl | $HO_2C$—$CH_2$— | Me | OMe | N | N | O |
| I-35 | OH | phenyl | $HO_2C$—$CH_2$— | ethyl | Me | N | N | O |
| I-36 | OH | phenyl | $HO_2C$—$CH_2$— | Me | ethyl | N | N | O |
| I-37 | OH | phenyl | $HO_2C$—$CH_2$— | Me | Me | N | N | O |

TABLE I-continued

[sic]

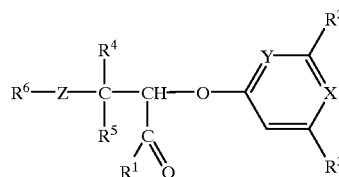

| No. | R¹ | R⁴, R⁵ | R⁶ | R³ | R² | X | Y | Z |
|---|---|---|---|---|---|---|---|---|
| I-38 | OH | phenyl | $HO_2C-CH_2-$ | OMe | SMe | N | N | O |
| I-39 | OH | phenyl | $HO-CH_2-(CH-OH)-CH_2-$ | OMe | OMe | N | N | O |
| I-40 | OH | phenyl | $HO-CH_2-(CH-OH)-CH_2-$ | OMe | Me | N | N | O |
| I-41 | OH | phenyl | $HO-CH_2-(CH-OH)-CH_2-$ | Me | OMe | N | N | O |
| I-42 | OH | phenyl | $HO-CH_2-(CH-OH)-CH_2-$ | ethyl | Me | N | N | O |
| I-43 | OH | phenyl | $HO-CH_2-(CH-OH)-CH_2-$ | Me | ethyl | N | N | O |
| I-44 | OH | phenyl | $HO-CH_2-(CH-OH)-CH_2-$ | Me | Me | N | N | O |
| I-45 | OH | phenyl | $HO-CH_2-(CH-OH)-CH_2-$ | OMe | SMe | N | N | O |
| I-46 | OH | phenyl | $HO-CH_2-(CH-OH)-CH_2-$ | OMe | $CF_3$ | N | N | O |
| I-47 | OH | phenyl | $HO-CH_2-(CH-OH)-CH_2-$ | OMe | OMe | N | N | S |
| I-48 | OH | phenyl | $HO-CH_2-(CH-OH)-CH_2-$ | OMe | Me | N | N | S |
| I-49 | OH | phenyl | $HO-CH_2-(CH-OH)-CH_2-$ | Me | OMe | N | N | S |
| I-50 | OH | phenyl | $HO-CH_2-(CH-OH)-CH_2-$ | ethyl | Me | N | N | S |
| I-51 | OH | phenyl | $HO-CH_2-CH_2-$ | OMe | OMe | N | N | S |
| I-52 | OH | phenyl | $HO-CH_2-CH_2-$ | OMe | Me | N | N | S |
| I-53 | OH | phenyl | $HO-CH_2-CH_2-$ | Me | OMe | N | N | S |
| I-54 | OH | phenyl | $HO-CH_2-CH_2-$ | ethyl | Me | N | N | S |
| I-55 | OH | phenyl | $HO-(CH_2)_3-$ | OMe | OMe | N | N | O |
| I-56 | OH | phenyl | $HO-(CH_2)_3-$ | OMe | Me | N | N | O |
| I-57 | OH | phenyl | $HO-(CH_2)_3-$ | Me | OMe | N | N | O |
| I-58 | OH | phenyl | $HO-(CH_2)_3-$ | ethyl | Me | N | N | O |
| I-59 | OH | phenyl | $HO-(CH_2)_3-$ | Me | ethyl | N | N | O |
| I-60 | OH | phenyl | $HO-(CH_2)_3-$ | Me | Me | N | N | O |
| I-61 | OH | phenyl | $HO-(CH_2)_3-$ | OMe | SMe | N | N | O |
| I-62 | OH | phenyl | $HO-(CH_2)_3-$ | OMe | $CF_3$ | N | N | O |
| I-63 | OH | phenyl | $HO-(CH_2)_3-$ | OMe | OMe | N | N | S |
| I-64 | OH | phenyl | $HO-(CH_2)_3-$ | OMe | Me | N | N | S |
| I-65 | OH | phenyl | $HO-(CH_2)_3-$ | Me | OMe | N | N | S |
| I-66 | OH | phenyl | $HO-(CH_2)_3-$ | ethyl | Me | N | N | S |
| I-67 | OH | phenyl | n-propyl | OMe | OMe | N | N | O |
| I-68 | OH | phenyl | n-propyl | OMe | Me | N | N | O |
| I-69 | OH | phenyl | n-propyl | Me | OMe | N | N | O |
| I-70 | OH | phenyl | n-propyl | ethyl | Me | N | N | O |
| I-71 | OH | phenyl | n-propyl | Me | ethyl | N | N | O |
| I-72 | OH | phenyl | n-propyl | Me | Me | N | N | O |
| I-73 | OH | phenyl | n-propyl | OMe | SMe | N | N | O |
| I-74 | OH | phenyl | n-propyl | OMe | $CF_3$ | N | N | O |
| I-75 | OH | phenyl | n-propyl | OMe | OMe | N | N | S |
| I-76 | OH | phenyl | n-propyl | OMe | Me | N | N | S |
| I-77 | OH | phenyl | n-propyl | Me | OMe | N | N | S |
| I-78 | OH | phenyl | n-propyl | ethyl | Me | N | N | S |
| I-79 | OH | phenyl | iso-propyl | OMe | OMe | N | N | O |
| I-80 | OH | phenyl | iso-propyl | OMe | Me | N | N | O |
| I-81 | OH | phenyl | iso-propyl | Me | OMe | N | N | O |
| I-82 | OH | phenyl | iso-propyl | ethyl | Me | N | N | O |
| I-83 | OH | phenyl | iso-propyl | Me | ethyl | N | N | O |
| I-84 | OH | phenyl | iso-propyl | Me | Me | N | N | O |
| I-85 | OH | phenyl | iso-propyl | OMe | SMe | N | N | O |
| I-86 | OH | phenyl | iso-propyl | OMe | $CF_3$ | N | N | O |
| I-87 | OH | phenyl | iso-propyl | OMe | OMe | N | N | S |
| I-88 | OH | phenyl | iso-propyl | OMe | Me | N | N | S |
| I-89 | OH | phenyl | iso-propyl | Me | OMe | N | N | S |
| I-90 | OH | phenyl | iso-propyl | ethyl | Me | N | N | S |
| I-91 | OH | phenyl | methyl | $CF_3$ | tert-Butyl | N | N | O |
| I-92 | OH | phenyl | methyl | $CF_3$ | OMe | N | N | O |
| I-93 | OH | phenyl | methyl | SMe | OMe | N | N | O |
| I-94 | OH | phenyl | methyl | $CF_3$ | Me | N | N | O |
| I-95 | OH | phenyl | methyl | Me | $CF_3$ | N | N | O |
| I-96 | OH | phenyl | benzyl | OMe | Me | N | N | O |
| I-97 | OH | phenyl | benzyl | Me | OMe | N | N | O |
| I-98 | OH | phenyl | benzyl | ethyl | Me | N | N | O |
| I-99 | OH | phenyl | benzyl | Me | ethyl | N | N | O |
| I-100 | OH | phenyl | benzyl | Me | Me | N | N | O |
| I-101 | OH | phenyl | benzyl | OMe | OMe | N | N | O |

TABLE I-continued

[sic]

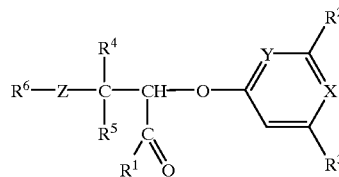

I

| No. | $R^1$ | $R^4, R^5$ | $R^6$ | $R^3$ | $R^2$ | X | Y | Z |
|---|---|---|---|---|---|---|---|---|
| I-102 | OH | phenyl | phenyl | OMe | Me | N | N | O |
| I-103 | OH | phenyl | phenyl | Me | OMe | N | N | O |
| I-104 | OH | phenyl | phenyl | ethyl | Me | N | N | O |
| I-105 | OH | phenyl | phenyl | Me | ethyl | N | N | O |
| I-106 | OH | phenyl | phenyl | Me | Me | N | N | O |
| I-107 | OH | phenyl | phenyl | OMe | OMe | N | N | O |
| I-108 | OH | phenyl | 4-OMe-benzyl | OMe | Me | N | N | O |
| I-109 | OH | phenyl | 4-OMe-benzyl | Me | OMe | N | N | O |
| I-110 | OH | phenyl | 4-OMe-benzyl | ethyl | Me | N | N | O |
| I-111 | OH | phenyl | 4-OMe-benzyl | Me | ethyl | N | N | O |
| I-112 | OH | phenyl | 4-OMe-benzyl | Me | Me | N | N | O |
| I-113 | OH | phenyl | 4-OMe-benzyl | OMe | OMe | N | N | O |
| I-114 | OH | phenyl | 4-Cl-benzyl | OMe | Me | N | N | O |
| I-115 | OH | phenyl | 4-Cl-benzyl | Me | OMe | N | N | O |
| I-116 | OH | phenyl | 4-Cl-benzyl | ethyl | Me | N | N | O |
| I-117 | OH | phenyl | 4-Cl-benzyl | Me | ethyl | N | N | O |
| I-118 | OH | phenyl | 4-Cl-benzyl | Me | Me | N | N | O |
| I-119 | OH | phenyl | 4-Cl-benzyl | OMe | OMe | N | N | O |
| I-120 | OH | cyclohexyl | methyl | OMe | OMe | N | N | O |
| I-121 | OH | cyclohexyl | methyl | OMe | Me | N | N | O |
| I-122 | OH | cyclohexyl | methyl | Me | OMe | N | N | O |
| I-123 | OH | cyclohexyl | methyl | ethyl | Me | N | N | O |
| I-124 | OH | cyclohexyl | methyl | Me | ethyl | N | N | O |
| I-125 | OH | cyclohexyl | methyl | Me | $CF_3$ | N | N | O |
| I-126 | OH | cyclohexyl | ethyl | OMe | Me | N | N | O |
| I-127 | OH | cyclohexyl | ethyl | Me | OMe | N | N | O |
| I-128 | OH | cyclohexyl | ethyl | ethyl | Me | N | N | O |
| I-129 | OH | cyclohexyl | ethyl | OMe | ethyl | N | N | O |
| I-130 | OH | cyclohexyl | HO—$CH_2$—$CH_2$— | OMe | Me | N | N | O |
| I-131 | OH | cyclohexyl | HO—$CH_2$—$CH_2$— | Me | OMe | N | N | O |
| I-132 | OH | cyclohexyl | HO—$CH_2$—$CH_2$— | ethyl | Me | N | N | O |
| I-133 | OH | cyclohexyl | HO—$CH_2$—$CH_2$— | Me | ethyl | N | N | O |
| I-134 | OH | cyclohexyl | HO—$CH_2$—$CH_2$— | Me | Me | N | N | O |
| I-135 | OH | 4-fluorophenyl | methyl | OMe | OMe | N | N | O |
| I-136 | OH | 4-fluorophenyl | methyl | OMe | Me | N | N | O |
| I-137 | OH | 4-fluorophenyl | methyl | Me | OMe | N | N | O |
| I-138 | OH | 4-fluorophenyl | methyl | ethyl | Me | N | N | O |
| I-139 | OH | 4-fluorophenyl | methyl | Me | ethyl | N | N | O |
| I-140 | OH | 4-fluorophenyl | methyl | Me | $CF_3$ | N | N | O |
| I-141 | OH | 4-fluorophenyl | ethyl | OMe | Me | N | N | O |
| I-142 | OH | 4-fluorophenyl | ethyl | Me | OMe | N | N | O |
| I-143 | OH | 4-fluorophenyl | ethyl | Me | Et | N | N | O |
| I-144 | OH | 4-fluorophenyl | ethyl | OMe | ethyl | N | N | O |
| I-145 | OH | 4-fluorophenyl | HO—$CH_2$—$CH_2$— | OMe | Me | N | N | O |
| I-146 | OH | 4-fluorophenyl | HO—$CH_2$—$CH_2$— | Me | OMe | N | N | O |
| I-147 | OH | 4-fluorophenyl | HO—$CH_2$—$CH_2$— | ethyl | Me | N | N | O |
| I-148 | OH | 4-fluorophenyl | HO—$CH_2$—$CH_2$— | Me | ethyl | N | N | O |
| I-149 | OH | 4-fluorophenyl | HO—$CH_2$—$CH_2$— | Me | Me | N | N | O |
| I-150 | OH | 4-fluorophenyl | HO—$CH_2$—$CH_2$— | OMe | OMe | N | N | O |
| I-151 | OH | 4-chlorophenyl | methyl | OMe | Me | N | N | O |
| I-152 | OH | 4-chlorophenyl | methyl | Me | OMe | N | N | O |
| I-153 | OH | 4-chlorophenyl | methyl | ethyl | Me | N | N | O |
| I-154 | OH | 4-chlorophenyl | methyl | Me | ethyl | N | N | O |
| I-155 | QH | 4-chlorophenyl | methyl | Me | $CF_3$ | N | N | O |
| I-156 | OH | 4-chlorophenyl | ethyl | OMe | Me | N | N | O |
| I-157 | OH | 4-chlorophenyl | ethyl | Me | OMe | N | N | O |
| I-158 | OH | 4-chlorophenyl | ethyl | Me | Et | N | N | O |
| I-159 | OH | 4-chlorophenyl | ethyl | OMe | ethyl | N | N | O |
| I-160 | OH | 4-chlorophenyl | HO—$CH_2$—$CH_2$— | OMe | Me | N | N | O |
| I-161 | OH | 4-chlorophenyl | HO—$CH_2$—$CH_2$— | Me | OMe | N | N | O |
| I-162 | OH | 4-chlorophenyl | HO—$CH_2$—$CH_2$— | ethyl | Me | N | N | O |
| I-163 | OH | 4-chlorophenyl | HO—$CH_2$—$CH_2$— | Me | ethyl | N | N | O |
| I-164 | OH | 4-chlorophenyl | HO—$CH_2$—$CH_2$— | Me | Me | N | N | O |
| I-165 | OH | 4-methylphenyl | methyl | Me | Me | N | N | O |

TABLE I-continued

[sic]

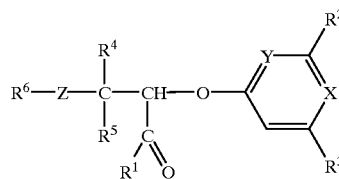

I

| No. | R¹ | R⁴, R⁵ | R⁶ | R³ | R² | X | Y | Z |
|---|---|---|---|---|---|---|---|---|
| I-166 | OH | phenyl | methyl | CH₃ | CH=CH—CH=CH—C | | N | O |
| I-167 | OH | phenyl | methyl | H | CH=CH—CH=CH—C | | N | O |
| I-168 | OH | phenyl | methyl | Me | Me | CH | N | O |
| I-169 | OH | phenyl | methyl | Me | ethyl | CH | N | O |
| I-170 | OH | phenyl | methyl | ethyl | Me | CH | N | O |
| I-171 | OH | phenyl | methyl | OMe | Me | CH | N | O |
| I-172 | OH | phenyl | methyl | Me | CH₂—CH₂—CH₂—C | | N | O |
| I-173 | OH | phenyl | methyl | ethyl | CH₂—CH₂—CH₂—C | | N | O |
| I-174 | OH | phenyl | methyl | CF₃ | Me | CH | N | O |
| I-175 | OH | phenyl | methyl | CF₃ | ethyl | CH | N | O |
| I-176 | OH | phenyl | ethyl | CH₃ | CH=CH—CH=CH—C | | N | O |
| I-177 | OH | phenyl | ethyl | H | CH=CH—CH=CH—C | | N | O |
| I-178 | OH | phenyl | ethyl | Me | Me | CH | N | O |
| I-179 | OH | phenyl | ethyl | Me | ethyl | CH | N | O |
| I-180 | OH | phenyl | ethyl | ethyl | Me | CH | N | O |
| I-181 | OH | phenyl | ethyl | OMe | Me | CH | N | O |
| I-182 | OH | phenyl | ethyl | Me | CH₂—CH₂—CH₂—C | | N | O |
| I-183 | OH | phenyl | ethyl | ethyl | CH₂—CH₂—CH₂—C | | N | O |
| I-184 | OH | phenyl | ethyl | CF₃ | Me | CH | N | O |
| I-185 | OH | phenyl | ethyl | CF₃ | ethyl | CH | N | O |
| I-186 | OH | phenyl | n-propyl | CH₃ | CH=CH—CH=CH—C | | N | O |
| I-187 | OH | phenyl | n-propyl | H | CH=CH—CH=CH—C | | N | O |
| I-188 | OH | phenyl | n-propyl | Me | Me | CH | N | O |
| I-189 | OH | phenyl | n-propyl | Me | ethyl | CH | N | O |
| I-190 | OH | phenyl | n-propyl | ethyl | Me | CH | N | O |
| I-191 | OH | phenyl | n-propyl | OMe | Me | CH | N | O |
| I-192 | OH | phenyl | n-propyl | Me | CH₂—CH₂—CH₂—C | | N | O |
| I-193 | OH | phenyl | n-propyl | ethyl | CH₂—CH₂—CH₂—C | | N | O |
| I-194 | OH | phenyl | n-propyl | CF₃ | Me | CH | N | O |
| I-195 | OH | phenyl | n-propyl | CF₃ | ethyl | CH | N | O |
| I-196 | OH | phenyl | HO—CH₂—CH₂— | CH₃ | CH=CH—CH=CH—C | | N | O |
| I-197 | OH | phenyl | HO—CH₂—CH₂— | H | CH=CH—CH=CH—C | | N | O |
| I-198 | OH | phenyl | HO—CH₂—CH₂— | Me | Me | CH | N | O |
| I-199 | OH | phenyl | HO—CH₂—CH₂— | Me | ethyl | CH | N | O |
| I-200 | OH | phenyl | HO—CH₂—CH₂— | ethyl | Me | CH | N | O |
| I-201 | OH | phenyl | HO—CH₂—CH₂— | OMe | Me | CH | N | O |
| I-202 | OH | phenyl | HO—CH₂—CH₂— | Me | CH₂—CH₂—CH₂—C | | N | O |
| I-203 | OH | phenyl | HO—CH₂—CH₂— | ethyl | CH₂—CH₂—CH₂—C | | N | O |
| I-204 | OH | phenyl | HO—CH₂—CH₂— | CF₃ | Me | CH | N | O |
| I-205 | OH | phenyl | HO—CH₂—CH₂— | CF₃ | ethyl | CH | N | O |
| I-206 | OH | phenyl | HOOC—CH₂—CH₂— | CH₃ | CH=CH—CH=CH—C | | N | O |
| I-207 | OH | phenyl | HOOC—CH₂—CH₂— | H | CH=CH—CH=CH—C | | N | O |
| I-208 | OH | phenyl | HOOC—CH₂—CH₂— | Me | Me | CH | N | O |
| I-209 | OH | phenyl | HOOC—CH₂—CH₂— | Me | ethyl | CH | N | O |
| I-210 | OH | phenyl | HOOC—CH₂—CH₂— | ethyl | Me | CH | N | O |
| I-211 | OH | phenyl | HOOC—CH₂—CH₂— | OMe | Me | CH | N | O |
| I-212 | OH | phenyl | HOOC—CH₂—CH₂— | Me | CH₂—CH₂—CH₂—C | | N | O |
| I-213 | OH | phenyl | HOOC—CH₂—CH₂— | ethyl | CH₂—CH₂—CH₂—C | | N | O |
| I-214 | OH | phenyl | HOOC—CH₂—CH₂— | CF₃ | Me | CH | N | O |
| I-215 | OH | phenyl | HOOC—CH₂—CH₂— | CF₃ | ethyl | CH | N | O |
| I-216 | OH | phenyl | HO—CH₂—(CH—OH)—CH₂— | Me | Me | CH | N | O |
| I-217 | OH | phenyl | HO—CH₂—(CH—OH)—CH₂— | Me | ethyl | CH | N | O |
| I-218 | OH | phenyl | HO—CH₂—(CH—OH)—CH₂— | ethyl | Me | CH | N | O |
| I-219 | OH | phenyl | HO—CH₂—(CH—OH)—CH₂— | OMe | Me | CH | N | O |
| t-220 | OH | phenyl | iso-propyl | Me | Me | CH | N | O |
| I-221 | OH | phenyl | iso-propyl | Me | ethyl | CH | N | O |
| I-222 | OH | phenyl | iso-propyl | ethyl | Me | CH | N | O |
| I-223 | OH | phenyl | iso-propyl | OMe | Me | CH | N | O |
| I-224 | OH | phenyl | methyl | Me | Me | CH | N | S |
| I-225 | OH | phenyl | methyl | Me | ethyl | CH | N | S |
| I-226 | OH | phenyl | methyl | ethyl | Me | CH | N | S |
| I-227 | OH | phenyl | methyl | OMe | Me | CH | N | S |
| I-228 | OH | 4-fluorophenyl | methyl | Me | Me | CH | N | O |
| I-229 | OH | 4-fluorophenyl | methyl | Me | ethyl | CH | N | O |

TABLE I-continued

[sic]

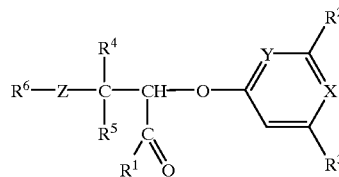

| No. | R$^1$ | R$^4$, R$^5$ | R$^6$ | R$^3$ | R$^2$ | X | Y | Z |
|---|---|---|---|---|---|---|---|---|
| I-230 | OH | 4-fluorophenyl | methyl | ethyl | Me | CH | N | O |
| I-231 | OH | 4-fluorophenyl | methyl | OMe | Me | CH | N | O |
| I-232 | OH | 4-fluorophenyl | methyl | CF$_3$ | Me | CH | N | O |
| I-233 | OH | 4-fluorophenyl | methyl | CF$_3$ | ethyl | CH | N | O |
| I-234 | OH | 4-fluorophenyl | HO—CH$_2$—CH$_2$— | Me | Me | CH | N | O |
| I-235 | OH | 4-fluorophenyl | HO—CH$_2$—CH$_2$— | Me | ethyl | CH | N | O |
| I-236 | OH | 4-fluorophenyl | HO—CH$_2$—CH$_2$— | ethyl | Me | CH | N | O |
| I-237 | OH | 4-fluorophenyl | HO—CH$_2$—CH$_2$— | OMe | Me | CH | N | O |
| I-238 | OH | 4-chlorophenyl | methyl | Me | Me | CH | N | O |
| I-239 | OH | 4-chlorophenyl | methyl | Me | ethyl | CH | N | O |
| I-240 | OH | 4-chlorophenyl | methyl | ethyl | Me | CH | N | O |
| I-241 | OH | 4-chlorophenyl | methyl | OMe | Me | CH | N | O |
| I-242 | OH | 4-chlorophenyl | methyl | CF$_3$ | Me | CH | N | O |
| I-243 | OH | 4-chlorophenyl | methyl | CF$_3$ | ethyl | CH | N | Q |
| I-244 | OH | 4-chlorophenyl | HO—CH$_2$—CH$_2$— | Me | Me | CH | N | O |
| I-245 | OH | 4-chlorophenyl | HO—CH$_2$—CH$_2$— | Me | ethyl | CH | N | O |
| I-246 | OH | 4-chlorophenyl | HO—CH$_2$—CH$_2$— | ethyl | Me | CH | N | O |
| I-247 | OH | 4-chlorophenyl | HO—CH$_2$—CH$_2$— | OMe | Me | CH | N | O |
| I-248 | OH | phenyl | ethyl | Me | Me | N | N | O |
| I-249 | OH | phenyl | ethyl | OMe | SMe | N | N | O |
| I-250 | OH | phenyl | ethyl | OMe | CF$_3$ | N | N | O |
| I-251 | OH | phenyl | methyl | OMe | OMe | N | CH | O |
| I-252 | OH | phenyl | methyl | OMe | Me | N | CH | O |
| I-253 | OH | phenyl | methyl | Me | Me | N | CH | O |
| I-254 | OH | phenyl | methyl | ethyl | Me | N | CH | O |
| I-255 | OH | phenyl | methyl | ethyl | ethyl | N | CH | O |
| I-256 | OH | phenyl | methyl | CF$_3$ | Me | N | CH | O |
| I-257 | OH | phenyl | methyl | CF$_3$ | ethyl | N | CH | O |
| I-258 | OH | phenyl | methyl | OMe | CF$_3$ | N | CH | O |
| I-259 | OH | phenyl | methyl | OMe | OMe | N | CH | S |
| I-260 | OH | phenyl | methyl | OMe | Me | N | CH | S |
| I-261 | OH | phenyl | methyl | Me | Me | N | CH | S |
| I-262 | OH | phenyl | methyl | ethyl | Me | N | CH | S |
| I-263 | OH | phenyl | ethyl | OMe | OMe | N | CH | O |
| I-264 | OH | phenyl | ethyl | OMe | Me | N | CH | O |
| I-265 | OH | phenyl | ethyl | Me | Me | N | CH | O |
| I-266 | OH | phenyl | ethyl | ethyl | Me | N | CH | O |
| I-267 | OH | phenyl | HO—CH$_2$—CH$_2$— | OMe | OMe | N | CH | O |
| I-268 | OH | phenyl | HO—CH$_2$—CH$_2$— | OMe | Me | N | CH | O |
| I-269 | OH | phenyl | HO—CH$_2$—CH$_2$— | Me | Me | N | CH | O |
| I-270 | OH | phenyl | HO—CH$_2$—CH$_2$— | ethyl | Me | N | CH | O |
| I-271 | OH | phenyl | HO—CH$_2$—(CH—OH)—CH$_2$— | OMe | OMe | N | CH | O |
| I-272 | OH | phenyl | HO—CH$_2$—(CH—OH)—CH$_2$— | OMe | Me | N | CH | O |
| I-273 | OH | phenyl | HO—CH$_2$—(CH—OH)—CH$_2$— | Me | Me | N | CH | O |
| I-274 | OH | phenyl | HO—CH$_2$—(CH—OH)—CH$_2$— | ethyl | Me | N | CH | O |
| I-275 | OH | phenyl | HOOC—CH$_2$—CH$_2$— | OMe | OMe | N | CH | O |
| I-276 | OH | phenyl | HOOC—CH$_2$—CH$_2$— | OMe | Me | N | CH | O |
| I-277 | OH | phenyl | HOOC—CH$_2$—CH$_2$— | Me | Me | N | CH | O |
| I-278 | OH | phenyl | HOOC—CH$_2$—CH$_2$— | ethyl | Me | N | CH | O |
| I-279 | OH | phenyl | propyl | OMe | OMe | N | CH | O |
| I-280 | OH | phenyl | propyl | OMe | Me | N | CH | O |
| I-281 | OH | phenyl | propyl | Me | Me | N | CH | O |
| I-282 | OH | phenyl | propyl | ethyl | Me | N | CH | O |
| I-283 | OH | phenyl | 4-OMe-benzyl | OMe | OMe | N | CH | O |
| I-284 | OH | phenyl | 4-OMe-benzyl | OMe | Me | N | CH | O |
| I-285 | OH | phenyl | 4-OMe-benzyl | Me | Me | N | CH | O |
| I-286 | OH | phenyl | 4-OMe-benzyl | ethyl | Me | N | CH | O |
| I-287 | OH | 4-fluorophenyl | methyl | OMe | OMe | N | CH | O |
| I-288 | OH | 4-fluorophenyl | methyl | OMe | Me | N | CH | O |
| I-289 | OH | 4-fluorophenyl | methyl | Me | Me | N | CH | O |
| I-290 | OH | 4-fluorophenyl | methyl | ethyl | Me | N | CH | O |
| I-291 | OH | 4-fluorophenyl | ethyl | OMe | OMe | N | CH | O |
| I-292 | OH | 4-fluorophenyl | ethyl | OMe | Me | N | CH | O |
| I-293 | OH | 4-fluorophenyl | ethyl | Me | Me | N | CH | O |

TABLE I-continued

[sic]

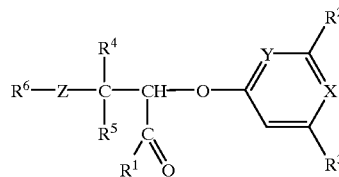

| No. | R¹ | R⁴, R⁵ | R⁶ | R³ | R² | X | Y | Z |
|---|---|---|---|---|---|---|---|---|
| I-294 | OH | 4-fluorophenyl | ethyl | ethyl | Me | N | CH | O |
| I-295 | OH | 4-fluorophenyl | HO—CH₂—CH₂— | OMe | OMe | N | CH | O |
| I-296 | OH | 4-fluorophenyl | HO—CH₂—CH₂— | OMe | Me | N | CH | O |
| I-297 | OH | 4-fluorophenyl | HO—CH₂—CH₂— | Me | Me | N | CH | O |
| I-298 | OH | 4-fluorophenyl | HO—CH₂—CH₂— | ethyl | Me | N | CH | O |
| I-299 | OH | 4-chlorophenyl | methyl | OMe | OMe | N | CH | O |
| I-300 | OH | 4-chlorophenyl | methyl | OMe | Me | N | CH | O |
| I-301 | OH | 4-chlorophenyl | methyl | Me | Me | N | CH | O |
| I-302 | OH | 4-chlorophenyl | methyl | ethyl | Me | N | CH | O |
| I-303 | OH | 4-chlorophenyl | ethyl | OMe | OMe | N | CH | O |
| I-304 | OH | 4-chlorophenyl | ethyl | OMe | Me | N | CH | O |
| I-305 | OH | 4-chlorophenyl | ethyl | Me | Me | N | CH | O |
| I-306 | OH | 4-chlorophenyl | ethyl | ethyl | Me | N | CH | O |
| I-307 | OH | 4-chlorophenyl | HO—CH₂—CH₂— | OMe | OMe | N | CH | O |
| I-308 | OH | 4-chlorophenyl | HO—CH₂—CH₂— | OMe | Me | N | CH | O |
| I-309 | OH | 4-chlorophenyl | HO—CH₂—CH₂— | Me | Me | N | CH | O |
| I-310 | OH | 4-chlorophenyl | HO—CH₂—CH₂— | ethyl | Me | N | CH | O |

The compounds of the present invention provide a novel therapeutic potential for the treatment of hypertension, pulmonary hypertension, myocardial infarct, angina pectoris, acute kidney failure, renal insufficiency, cerebral vasospasms, cerebral ischemia, subarachnoidal hemorrhages, migraine, asthma, atherosclerosis, endotoxic shock, endotoxin-induced organ failure, intravascular coagulation, restenosis after angioplasty, benign prostate hyperplasia, or hypertension or kidney failure caused by ischemia or intoxication, and of cancers, especially prostate cancer and skin cancer. The invention further relates to the combination of compounds of the formula I with inhibitors of the renin-angiotensin system (RAS). RAS inhibitors are disclosed in, for example, EP 634 175.

The combinations according to the invention are suitable for treating disorders for which compounds of the formula I also shows efficacy on their own, especially for treating hypertension and chronic heart failure.

The good effect of the compounds can be shown in the following tests:
Receptor Binding Studies Cloned human $ET_A$ receptor-expressing CHO cells and guinea pig cerebellar membranes with >60% $ET_B$ compared with $ET_A$ receptors were used for binding studies.
Membrane Preparation The $ET_A$ receptor-expressing CHO cells were grown in $F_{12}$ medium containing 10% fetal calf serum, 1% glutamine, 100 E/ml penicillin and 0.2% streptomycin (Gibco BRL, Gaithersburg, Md., USA). After 48 h, the cells were washed with PBS and incubated with 0.05% trypsin-containing PBS for 5 min. Neutralization was then carried out with $F_{12}$ medium and the cells were collected by centrifugation at 300×g. To lyse the cells, the pellet was briefly washed with lysis buffer (5 mM tris-HCl, pH 7.4 with 10% glycerol) and then incubated at a concentration of $10^7$ cells/ml of lysis buffer at 4° C. for 30 min. The membranes were centrifuged at 20,000×g for 10 min, and the pellet was stored in liquid nitrogen.

Guinea pig cerebella were homogenized in a Potter-Elvejhem homogenizer and were obtained by differential centrifugation at 1,000×g for 10 min and repeated centrifugation of the supernatent at 20,000×g for 10 min.
Binding Assays For the $ET_A$ and $ET_B$ receptor binding assay, the membranes were suspended in incubation buffer (50 mM tris-HCl, pH 7.4 with 5 mM of $MnCl_2$, 40 μg/ml bacitracin and 0.2% BSA) at a concentration of 50 μg of protein per assay mixture and incubated with 25 pM [125I ]-$ET_1$ ($ET_A$ receptor assay) or 25 pM [125I]-$RZ_3$ ($ET_B$ receptor assay) in the presence and absence of test substance. The nonspecific binding was determined with $10^{-7}$ M $ET_1$. After 30 min, filtration was carried out through GF/B glass fiber filters (Whatman, England) in a Skatron cell collector (Skatron, Lier, Norway) to separate free and bound radioligands, and the filters were washed with ice-cold tris-HCl buffer, pH 7.4 with 0.2% BSA. The radioactivity collected on the filters was quantified using a Packard 2200 CA liquid scintillation counter.
Functional in Vitro Assay System to Look for Endothelin Receptor (Subtype A) Antagonists This assay system is a functional, cell-based assay for endothelin receptors. When certain cells are stimulated with endothelin 1 (ET1) they show an increase in the intracellular calcium concentration. This increase can be measured in intact cells loaded with calcium-sensitive dyes.

1-Fibroblasts which had been isolated from rats and in which an endogenous endothelin receptor of the A subtype had been detected were loaded with the fluorescent dye Fura 2-an as follows: after trypsinization, the cells were resuspended in buffer A (120 mM NaCl, 5 mM KCl, 1.5 mM $MgCl_2$, 1 mM $CaCl_2$, 25 mM HEPES, 10 mM glucose, pH 7.4) to a density of $2×10^6$/ml and incubated with Fura 2-am (2 μM), Pluronics [sic] F-127 (0.04%) and DMSO (0.2%) at 37° C. in the dark for 30 min. The cells were then washed twice with buffer A and resuspended at $2×10^6$/ml.

The fluorescence signal from $2×10^5$ cells per ml with Ex/Em 380/510 was recorded continuously at 30° C. The test substances and, after an incubation time of 3 min, ET1 were to the cells, the maximum change in the fluorescence was determined. The response of the cells to ET1 without previous addition of a test substance was used as control and was set equal to 100%.

Testing of ET Antagonists in Vivo

Male SD rats weighing 250–300 g were anesthetized with amobarbital, artificially ventilated, vagotomized and pithed. The carotid artery and jugular vein were cathetized.

In control animals, intravenous administration of 1 μg/kg ET1 led to a distinct rise in blood pressure which persisted for a lengthy period.

The test animals received an i.v. injection of the test compounds (1 ml/kg) 5 min before administration of ET1. To determine the ET-antagonistic properties, the rise in blood pressure in the test animals was compared with that in the control animals.

Endothelin-1 Induced "Sudden Death" in Mice

The principle of the test is the inhibition of the sudden heart death caused in mice by endothelin, which is probably induced by constriction of the coronary vessels, by pretreatment with endothelin receptor antagonists. Intravenous injection of 10 nmol/kg endothelin in a volume of 5 ml/kg of bodyweight results in death of the animals within a few minutes.

The lethal endothelin-1 dose is checked in each case on a small group of animals. If the test substance is administered intravenously, the endothelin-1 injection which was lethal in the reference group usually takes place 5 min thereafter. With other modes of administration, the times before administration are extended, where appropriate up to several hours.

The survival rate is recorded, and effective doses which protect 50% of the animals (ED 50) from endothelin-induced heart death for 24 h or longer are determined.

Function Test on Vessels for Endothelin Receptor Antagonists

Segments of rabbit aorta are, after an initial tension of 2 g and a relaxation time of 1 h in Krebs-Henseleit solution at 37° C. and pH 7.3–7.4, first induced to contract with $K^+$. After washing out, an endothelin dose-effect plot up to the maximum is constructed.

Potential endothelin antagonists are administered to other preparations of the same vessel 15 min before starting the endothelin dose-effect plot. The effects of the endothelin are calculated as % of the $K^{30}$-induced contraction. Effective endothelin antagonists result in a shift to the right in the endothelin dose-effect plot.

The compounds according to the invention can be administered orally or parenterally (subcutaneously, intravenously, intramuscularly, intraperotoneally in a conventional way. Administration can also take place with vapors or sprays through the nasopharyngeal space.

The dosage depends on the age, condition and weight of the patient and on the mode of administration. The daily dose of active substance is, as a rule, about 0.5 to 50 mg/kg of bodyweight on oral administration and about 0.1–10 mg/kg of bodyweight on parenteral administration.

The novel compounds can be used in conventional solid or liquid pharmaceutical forms, e.g. as uncoated or (film-) coated tablets, capsules, powders, granules, suppositories, solutions, ointments, creams or sprays. These are produced in a conventional way. The active substances can for this purpose be processed with conventional pharmaceutical aids such as tablet binders, bulking agents, preservatives, tablet disintegrants, flow regulators, plasticizers, wetting agents, dispersants, emulsifiers, solvents, release-slowing agents, antioxidants and/or propellant gases (cf. H. Sucker et al.: Pharmazeutische Technologie, Thieme-Verlag, Stuttgart, 1991). The forms obtained in this way normally contain from 0.1 to 90% by weight of active substance.

Synthesis Examples

EXAMPLE 1

Methyl 2-hydroxy-3-methoxy-3,3-diphenylpropionate 5 g (19.6 mmol) of methyl 3,3-diphenyl-2,3-epoxypropionate were dissolved in 50 ml of absolute methanol, and, at 0° C., 0.1 ml of boron trifluoride etherate was added. The mixture was stirred at 0° C. for 2 h and at room temperature for a further 12 h. The solvent was removed by distillation, the residue was taken up in ethyl acetate, and the solution was washed with sodium bicarbonate solution and water and dried over magnesium sulfate. After removal of the solvent by distillation, 5.5 g (88%) of a pale yellow oil remained.

EXAMPLE 2

Methyl 2-(2,6-dimethoxy-4-pyrimidyloxy)-3-methoxy-3,3-diphenyl-propionate 1.15 g (4 mmol) of methyl 2-hydroxy-3-methoxy-3,3-diphenyl-propionate were dissolved in 10 ml of dimethylformamide, and 276 mg (2 mmol) of potassium carbonate were added. Then 524 mg (3 mmol) of 2,6-dimethoxy-4-chloropyrimidine were added, and the mixture was stirred at 100° C. for 6 hours. It was then cautiously hydrolyzed with 10 ml of water, the pH was adjusted to 5 with citric acid and, after extraction with ethyl acetate, the organic phase was washed with water then dried over magnesium sulfate, and the solvent was removed by distillation. The oily residue (1.9 g) was chromatographed on silica gel, resulting in 617 mg of a slightly impure oil.

EXAMPLE 3

2-(2,6-Dimethoxy-4-pyrimidinyloxy)-3-methoxy-3,3-diphenyl-propionic acid 550 mg (1.3 mmol) of methyl 2-(2,6-dimethoxy-4-pyrimidinyl-oxy)-3-methoxy-3,3-diphenylpropionate were dissolved in 5 ml of dioxane, 2.6 ml of 1N KOH solution were added, and the mixture was stirred at 100° C. for 3 h. The solution was diluted with 300 ml of water and extracted with ethyl acetate to remove unreacted ester. The aqueous phase was then adjusted to pH 1–2 with dilute hydrochloric acid and was extracted with ethyl acetate. After drying over magnesium sulfate and removal of the solvent by distillation, the residual foam (425 mg) was purified by MPLC, resulting in 205 mg (40%) of product as foam.

EXAMPLE 4

Methyl 2-(4-methyl-2-quinolinyloxy)-3-methoxy-3,3-diphenyl-propionate 5.7 g (20 mmol) of Methyl 2-hydroxy-3-methoxy-3,3-diphenyl-propionate were dissolved in 90 ml of dimethylformamide, and 0.98 g (22 mmol) of sodium hydride (55% in oil) was added. After stirring for 15 minutes, 3.9 g (22 mmol) of 2-chloro-4-methylquinoline were added. The dark red solution was stirred at room temperature overnight, then cautiously hydrolyzed with 20 ml of water and subsequently extracted with ethyl acetate. The organic phase was washed with water, and dried over magnesium sulfate, and the solvent was removed by distillation. The residue (8.1 g) was then chromatographed on silica gel, resulting in 2.6 g of impure product as oil.

EXAMPLE 5

2-(4-Methyl-2-quinolinyloxy)-3-methoxy-3,3-diphenylpropionic acid 1.8 g (4.2 mmol) of methyl 2-(4-methyl-2-quinolinyloxy)-3-meth-oxy-3,3-diphenylpropionate were dissolved in 25 ml of dioxane, 8.4 ml of 1N KOH solution were added, and the mixture was stirred at 60° C. for 20 hours. The solution was diluted with 300 ml of water and extracted with ethyl acetate to remove unreacted ester and impurities. The aqueous phase was then adjusted to pH 1–2 with dilute hydrochloric acid and was extracted with ethyl acetate. Drying over magnesium sulfate and removal of the solvent by distillation resulted in 1.0 g of a foam. This was dissolved in a little ethyl acetate and left to stand at room temperature overnight, during which 265 mg of the product separated out as white crystals. Repetition of this procedure with the mother liquor afforded a further 166 mg of the product.

Total yield: 431 mg≐25%
Melting point: 131–133° C.
MS: M$^+$=413

EXAMPLE 6

Benzyl 2-(2-tert-butyl-6-trifluoromethyl-4-pyrimidinyloxy) -3-methoxy-3,3-diphenylpropionate 2.0 g (5.5 mmol) of benzyl 2-hydroxy-3-methoxy-3,3-diphenyl-propionate (see P44 36 851.8) were dissolved in 20 ml of dimethylformamide, and 0.76 g (5.5 mmol) of potassium carbonate was added. Then 1.32 g (5.5 mmol) of 2-tert-butyl-6-trifluoro-methyl-4-chloropyrimidine were added, and the mixture was stirred at room temperature overnight and then at 100° C. for 5 hours. To complete the reaction, a further 0.5 g of the pyrimidine and 0.5 g of NaH were added, and the mixture was stirred at 60° C. for a further 6 hours. Finally, it was poured into ice-water and extracted with ethyl acetate, the organic phase was washed with saturated NaCl solution and dried over magnesium sulfate, and the solvent was removed by distillation. The oily residue (3.5 g) crystallized in n-heptane/ethyl acetate (5%). The precipitate was filtered off with suction and dried.

Yield: 1.6 g≐52%
MS: M$^+$=564

EXAMPLE 7

2-(2-tert-Butyl-6-trifluoromethyl-4-pyrimidinyloxy)-3-methoxy-3,3-diphenylpropionic acid 2.0 g (5.5 mmol) of benzyl 2-(2-tert-butyl-6-trifluoro-methyl-4-pyrimidinyloxy)-3-methoxy-3,3-diphenylpropionate were dissolved in 250 ml of methanol, 120 mg of palladium on active carbon (5%) were added, and the mixture was stirred under hydrogen at room temperature for 2 hours. After hydrogen uptake ceased, the catalyst was removed by filtration through celite, and the solvent was stripped off in a rotary evaporator.

Yield: 1.0 g≐98%
1H-NMR (360 MHz, in CDCl$_3$, data in ppm): 1.35 (s, 9H); 3.3 (s, 3H); 6.3 (s, 1H); 6.8 (s, 1H); 7.15–7.45 (m, 10H)

The compounds listed in Table 1 can be prepared in a similar way.

EXAMPLE 8

Receptor binding data were measured for the compounds listed below using the binding assay described above.

The results are shown in Table 2.

TABLE 2

| Receptor binding data (K$_i$ values) | | |
| --- | --- | --- |
| Compound | ET$_A$ [µM] | ET$_B$ [µM] |
| I-1 | 0.038 | 8 |
| I-91 | 3.3 | >10 |
| I-166 | 0.5 | 4 |
| I-167 | 3 | >7 |

We claim:
1. A compound of the formula I

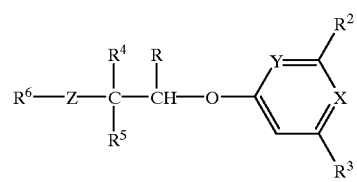

where R is a tetrazole, nitrile, or a group

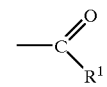

where R$^1$ has the following meanings:
b) a succinylimidoxy group;
c) a 5-membered heteroaromatic system linked via a nitrogen atom selected from the group consisting of pyrrolyl, pyrazolyl, imidazolyl and triazolyl, each of which may be unsubstituted or substituted by one or two halogen atoms or one or two C$_1$–C$_4$-alkyl or one or two C$_1$–C$_4$-alkoxy groups;
d) R$^1$ is furthermore a group

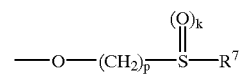

where k can assume the values 0, 1 and 2, p can assume the values 1, 2, 3 and 4, and R$^7$ is
C$_1$–C$_4$-alkyl, C$_3$–C$_7$-cycloalkyl, C$_3$–C$_6$-alkenyl, C$_3$–C$_6$-alkynyl or unsubstituted or substituted phenyl which can be substituted by one or more of the following radicals:
halogen, nitro, cyano, C$_1$–C$_4$-alkyl, C$_1$–C$_4$-haloalkyl, hydroxyl, C$_1$–C$_4$-alkoxy, C$_1$–C$_4$-alkylthio, mercapto, amino, C$_1$–C$_4$-alkylamino, C$_1$–C$_4$-dialkylamino;
e) R$^1$ is furthermore a radical OR$^8$ where R$^8$ is:
hydrogen, the cation of an alkali metal,
the cation of an alkaline earth metal, or a physiologically tolerated organic ammonium ion;
C$_3$–C$_8$-cycloalkyl,
a linear or branched C$_1$–C$_8$-alkyl,
CH$_2$-phenyl, which may be unsubstituted or substituted by one or more of the following radicals: halogen, nitro, cyano, C$_1$–C$_4$-alkyl, C$_1$–C$_4$-haloalkyl, hydroxyl, C$_1$–C$_4$-alkoxy, mercapto, C$_1$–C$_4$-alkylthio, amino, C$_1$–C$_4$-alkylamino, C$_1$–C$_4$-dialkylamino, a C$_3$–C$_6$-alkenyl or C$_3$–C$_6$-alkynyl group, it being possible for this group in turn to carry one to five halogen atoms;
R$^8$ can furthermore be a phenyl radical which can carry one to five halogen atoms and/or one to three of the following radicals: nitro, cyano, C$_1$–C$_4$-alkyl, C$_1$–C$_4$-haloalkyl, hydroxyl, C$_1$–C$_4$-alkoxy, mercapto, C$_1$–C$_4$-alkylthio, amino, C$_1$–C$_4$-alkylamino, C$_1$–C$_4$-dialkylamino;
a 5-membered heteroaromatic system which is linked via a nitrogen atom and contains one to three nitrogen atoms and which can carry one or two halogen atoms and/or one or two of the following radicals: $C_1$–$C_4$-alkyl, $C_1$–$C_4$-haloalkyl, $C_1$–$C_4$-alkoxy, phenyl, $C_1$–$C_4$-haloalkoxy and/or $C_1$–$C_4$-alkylthio;

f) $R^1$ is furthermore a radical

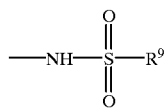

where $R^9$ is:

$C_1$–$C_4$-alkyl, $C_3$–$C_6$-alkenyl, $C_3$–$C_6$-alkynyl, $C_3$–$C_8$-cycloalkyl, it being possible for these radicals to carry a $C_1$–$C_4$-alkoxy, $C_1$–$C_4$-alkylthio and/or a phenyl radical; phenyl, unsubstituted or substituted;

g) $R^1$ can furthermore be a radical

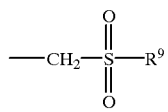

where $R^9$ has the abovementioned meaning;

h) $R^1$ can furthermore be

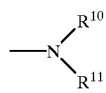

where $R^{10}$ and $R^{11}$ can be identical or different and have the following meanings:

hydrogen, $C_1$–$C_7$-alkyl, $C_3$–$C_7$-cycloalkyl, $C_3$–$C_7$-alkenyl, $C_3$–$C_7$-alkynyl, benzyl, phenyl, unsubstituted or substituted, as described above, or $R^{10}$ and $R^{11}$ together form a $C_4$–$C_7$-alkylene chain which is closed to form a ring, is unsubstituted or substituted by $C_1$–$C_4$-alkyl, and may contain an oxygen, sulfur or nitrogen atom;

the other substituents have the following meanings:

$R^2$ is hydrogen, hydroxyl, $NH_2$, $NH(C_1$–$C_4$-alkyl), $N(C_1$–$C_4$-alkyl)$_2$, halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, or $CR^2$ is linked to $CR^{12}$ as indicated below to form a 5- or 6-membered ring;

X is nitrogen or $CR^{12}$ where $R^{12}$ is hydrogen or $C_{1-5}$-alkyl, or $CR^{12}$ forms together with $CR^2$ or $CR^3$ a 5- or 6-membered alkylene or alkenylene ring which can be substituted by one or two $C_{1-4}$-alkyl groups and in which in each case one methylene group can be replaced by oxygen, sulfur, —NH or —N$C_{1-4}$-alkyl;

Y is nitrogen or methine;

$R^3$ is hydrogen, hydroxyl, $NH_2$, $NH(C_1$–$C_4$-alkyl), $N(C_1$–$C_4$-alkyl)$_2$, halogen, $C_1$–$C_4$-alkyl, $C_1$–$C_4$-haloalkyl, $C_1$–$C_4$-alkoxy, $C_1$–$C_4$-haloalkoxy, —NH—O—$C_{1-4}$-alkyl, $C_1$–$C_4$-alkylthio; or $CR^3$ is linked to $CR^{12}$ as indicated above to form a 5- or 6-membered ring;

$R^4$ and $R^5$ (which can be identical or different) are:

phenyl or naphthyl, each of which can be substituted by one or more of the following radicals: halogen, nitro, cyano, hydroxyl, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, amino, $C_1$–$C_4$-alkylamino or $C_1$–$C_4$-dialkylamino; or phenyl or naphthyl which are connected together in ortho positions by a direct linkage, a methylene, ethylene or ethenylene group, an oxygen or sulfur atom or an $SO_2$—, NH— or N-alkyl group, or $C_3$–$C_7$-cycloalkyl;

$R^6$ is hydrogen, $C_1$–$C_8$-alkyl, $C_3$–$C_6$-alkenyl, $C_3$–$C_6$-alkynyl or $C_3$–$C_8$-cycloalkyl, it being possible for each of these radicals to be substituted one or more times by: halogen, hydroxyl, mercapto, carboxyl, nitro, cyano, $C_1$–$C_4$-alkoxy, $C_3$–$C_6$-alkenyloxy, $C_3$–$C_6$-alkynyloxy, $C_1$–$C_4$-alkylthio, $C_1$–$C_4$-haloalkoxy, $C_1$–$C_4$-alkylcarbonyl, $C_1$–$C_4$-alkoxycarbonyl, $C_{3-8}$-alkylcarbonylalkyl, $C_1$–$C_4$-alkylamino, di-$C_1$–$C_4$-alkylamino, phenyl or phenoxy or phenyl, substituted one or more times by halogen, nitro, cyano, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio;

phenyl or naphthyl, each of which can be substituted by one or more of the following radicals: halogen, nitro, cyano, hydroxyl, amino, $C_1$–$C_4$-alkyl, $C_1$–$C_4$-haloalkyl, $C_1$–$C_4$-alkoxy, $C_1$–$C_4$-haloalkoxy, phenoxy, $C_1$–$C_4$-alkylthio, $C_1$–$C_4$-alkylamino, $C_1$–$C_4$-dialkylamino, dioxomethylene or dioxoethylene;

Z is sulfur or oxygen.

2. A compound as claimed in claim 1, wherein R is

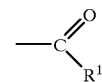

where $R^1$ is —$OR^8$, wherein $R^8$ is hydrogen.

3. A carboxylic acid derivative as claimed in claim 1, wherein at least one of the radicals $R^4$ and $R^5$ is phenyl.

4. A carboxylic acid derivative as claimed in claim 3, wherein $R^4$ and $R^5$ are both phenyl.

5. A carboxylic acid derivative as claimed in claim 3, wherein $R^6$ is $C_1$–$C_8$-alkyl, unsubstituted or substituted by OH or $C_1$–$C_4$-alkoxy, and Z is O.

6. A carboxylic acid derivative as claimed in claim 1, wherein X is CH.

7. A carboxylic acid derivative as claimed in claim 1 wherein at least one of the radicals X, Y is nitrogen (N).

8. A carboxylic acid derivative as claimed in claim 1, wherein at least one of the radicals $R^2$, $R^3$ is $C_1$–$C_4$-alkyl.

9. A method for treating hypertension, pulmonary hypertension, acute and chronic kidney failure, chronic heart failure, cerebral ischemia, restenosis after angioplasty, or prostate cancer comprising administering to a patient in need thereof an therapeutically effective amount of a compound as claimed in claim 1.

10. A composition containing a combination of a compound as claimed in claim 1 with an inhibitor of the renin-angiotensin system (RAS).

* * * * *

UNITED STATES PATENT AND TRADEMARK OFFICE
CERTIFICATE OF CORRECTION

PATENT NO.: 6,103,732

DATED: August 15, 2000

INVENTOR(S): AMBERG et al.

It is certified that error appears in the above-identified patent and that said Letters Patent is hereby corrected as shown below:

Col. 24, claim 3, line 41, "carboxylic acid derivative" should be --compound--.

Col. 24, claim 4, line 43, "carboxylic acid derivative" should be --compound--.

Col. 24, claim 5, line 45, "carboxylic acid derivative" should be --compound--.

Col. 24, claim 6, line 48, "carboxylic acid derivative" should be --compound--.

Col. 24, claim 7, line 50, "carboxylic acid derivative" should be --compound--.

Col. 24, claim 8, line 52, "carboxylic acid derivative" should be --compound--.

Signed and Sealed this

Tenth Day of April, 2001

*Attest:*

NICHOLAS P. GODICI

*Attesting Officer*     Acting Director of the United States Patent and Trademark Office